(12) United States Patent
Kobayashi

(10) Patent No.: US 7,985,096 B2
(45) Date of Patent: Jul. 26, 2011

(54) CONNECTOR WITH SWITCH

(75) Inventor: Katsuhiko Kobayashi, Yamanashi (JP)

(73) Assignee: Tyco Electronics Japan G.K., Kanagawa-ken (JP)

( * ) Notice: Subject to any disclaimer, the term of this patent is extended or adjusted under 35 U.S.C. 154(b) by 0 days.

(21) Appl. No.: 12/851,792

(22) Filed: Aug. 6, 2010

(65) Prior Publication Data

US 2010/0297879 A1 Nov. 25, 2010

Related U.S. Application Data

(63) Continuation of application No. PCT/JP2009/051568, filed on Jan. 30, 2009.

(30) Foreign Application Priority Data

Feb. 8, 2008 (JP) ................................. 2008-029472

(51) Int. Cl.
*H01R 13/58* (2006.01)
(52) U.S. Cl. .................................. 439/607.01; 439/188
(58) Field of Classification Search ............. 439/607.01, 439/607.31, 188; 200/51.1
See application file for complete search history.

(56) References Cited

U.S. PATENT DOCUMENTS

| 5,674,085 | A | * | 10/1997 | Davis et al. ................... 439/188 |
| 6,074,223 | A | * | 6/2000 | Huang ............................. 439/95 |
| 7,416,428 | B1 | * | 8/2008 | Hung et al. .................... 439/188 |
| 2006/0014434 | A1 | * | 1/2006 | Yamamoto et al. ........... 439/630 |

FOREIGN PATENT DOCUMENTS

| JP | 06-223924 | 8/1994 |
| JP | 09-147996 | 6/1997 |
| JP | 2001-291559 | 10/2001 |
| JP | 2005-242476 | 9/2005 |

OTHER PUBLICATIONS

International Search Report issued in co-pending International Application No. PCT/HP2009/051568, dated Mar. 9, 2009, 1 page.
PCT International Preliminary Report on Patentability and Written Opinion dated Sep. 7, 2010; 5 pages.

* cited by examiner

*Primary Examiner* — T C Patel
*Assistant Examiner* — Travis Chambers
(74) *Attorney, Agent, or Firm* — Barley Snyder LLC

(57) ABSTRACT

A connector includes an insulating housing, a metal shell that covers the insulative housing, and a switch. The switch includes a fixed contact and a movable contact. The fixed contact is formed by partially bending a rear end of a top surface of a metal shell downward. The metal shell covers an insulating housing to be mated with a mating connector. The movable contact extends while having a fixed end held by the insulating housing, and bifurcates at an approximate midpoint of the movable contact. The movable contact has, at one free end, an attachment section that abuts a mating connector approaching in a mating direction and a contacting section, at an opposite free end, that contacts the fixed contact when the attachment section is pushed by the mating connector.

20 Claims, 5 Drawing Sheets

CONNECTOR WITH SWITCH

CROSS-REFERENCE TO RELATED APPLICATIONS

This application is a continuation of PCT International Application No. PCT/JP2009/051568, filed Jan. 30, 2009, which claims priority under 35 U.S.C. §119 to Japanese Patent Application No. 2008-029472, filed Feb. 8, 2008.

FIELD OF THE INVENTION

The present invention relates to a connector, and in particular to a connector with a switch that detects mating with a mating connector.

BACKGROUND

Conventionally, there is known a connector having a switch that detects mating with a mating connector. This switch includes a pair of contacts made of a conductive members. A device provided with the connector with the switch electrically operates in response to detection of mating, with the mating connector by contact or separation between the pair of contacts included in the switch.

An example of such a connector with the switch, there is a connector with a circuit selector switch that includes a spring conductor and a fixed conductor (for example, see Japanese Patent Laid-Open No. H06-223924).

Further, for example, there is disclosed a card connector having a detection switch that includes a first and a second contact (for example, see Japanese Patent Laid-Open No. 2001-291559). The first contact is formed by bending a part of the rear end of a metal shell. The second contact includes, at a main part, a tine and a support section. The tine attaches to an attachment member of a circuit board or the like, while the support section is press-fitted into an insulating housing. The second contact includes a support arm extending from the main part in a direction opposite to the tine, and a contact arm extending from the support arm in the same direction as that of the support section. The contact arm of the second contact is formed such that a middle part is curved to be shaped approximately like a sign "L." Further, the support arm and the contact arm of the second contact have elasticity, and are formed like a cantilever by having the main part serving as a fixed end.

In the connector with the circuit selector switch disclosed in Japanese Patent Laid-Open No. H06-223924, both the spring conductor and the fixed conductor that are components of the switch are provided as separate components from the connector components, other than these conductors. As a result, there are a large number of components. Therefore, according to this connector with the circuit selector switch, it is difficult to manufacture this type of connector with the circuit selector switch at a low cost.

In the card connector disclosed in Japanese Patent Laid-Open No. 2001-291559, the first contact of the detection switch is formed by a part of the shell and thus, the number of components is smaller than the connector with the circuit selector switch disclosed in Japanese Patent Laid-Open No. H06-223924. However, in the second contact of this card connector, the support arm and the contact arm having elasticity are poor in flexibility because of the cantilever shape, whose both ends are supported. More specifically, the cantilever shape in which a contact point between the main part and the first contact serves as a fixed end at the time of contact with the first contact. Accordingly, an amount of displacement of the contact arm realized by only the flexibility of the support arm and the contact arm is insufficient and therefore, the first contact to be contacted by the contact arm also needs flexibility in order to supplement this insufficiency of the amount of displacement. In other words, according to this card connector, it is necessary to provide flexible space of the first contact in addition to flexible space of the second contact. Thus, according to this card connector, it is difficult to minimize space in the switch and reduce the size of the connector.

Further, there is a possibility that the contact arm, which as poor flexibility, may plastically deform upon repeated use. Furthermore, there is a possibility that when the contact arm which is poor in flexibility contacts the first contact arm, the first contact arm may be damaged by the contact arm. Therefore, there is such a problem that the card connector is poor in durability and contact reliability.

SUMMARY

In view of the foregoing circumstances, it is an object of the present invention to provide a connector having a switch, which minimizes the cost and size reduction of the connecter, as well as having high durability and contact reliability.

According to the present invention, the connector includes an insulating housing, a metal shell that covers the housing, and a switch. The switch includes a fixed contact and a movable contact. The fixed contact being formed by a part of the shell, while the movable contact includes a fixed end being held by the housing. The movable contact further includes a bifurcation part at an approximate midpoint of the movable contact that bifurcates into an attachment section and a contacting section.

BRIEF DESCRIPTION OF THE DRAWINGS

The invention is described in more detail in the following with reference to the embodiments shown in the drawings. Similar or corresponding details in the Figures are provided with the same reference numerals. The invention will be described in detail with reference to the following figures of which.

DETAILED DESCRIPTION OF THE EMBODIMENT(S)

Embodiments of the invention will be described below with reference to the drawings.

Figure 1:
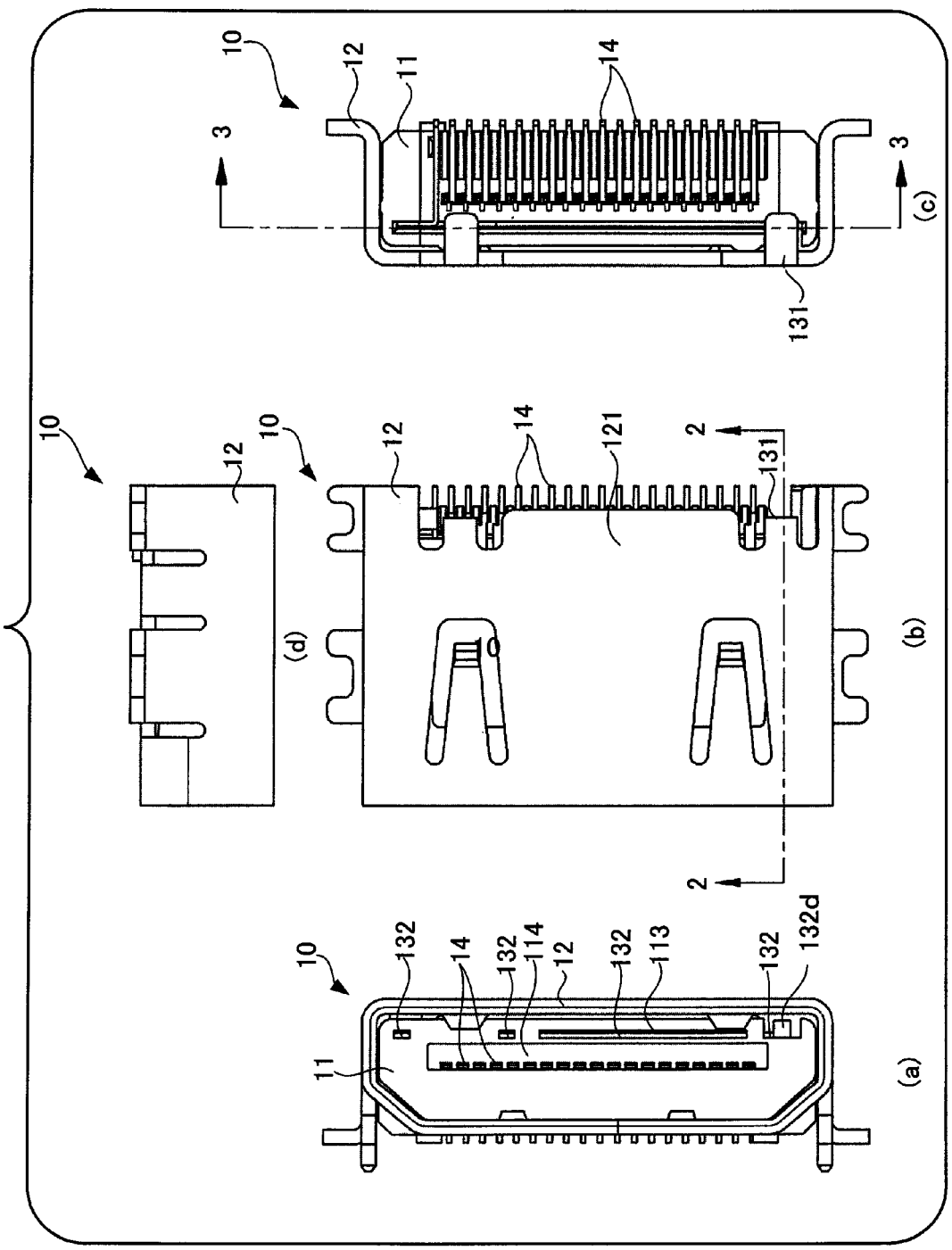
FIG. 1a is a front view of a connector with a switch according to the invention.
FIG. 1b is a top view of the connector according to the invention.
FIG. 1c is a rear view of a connector with a switch according to the invention.
Figure 2:
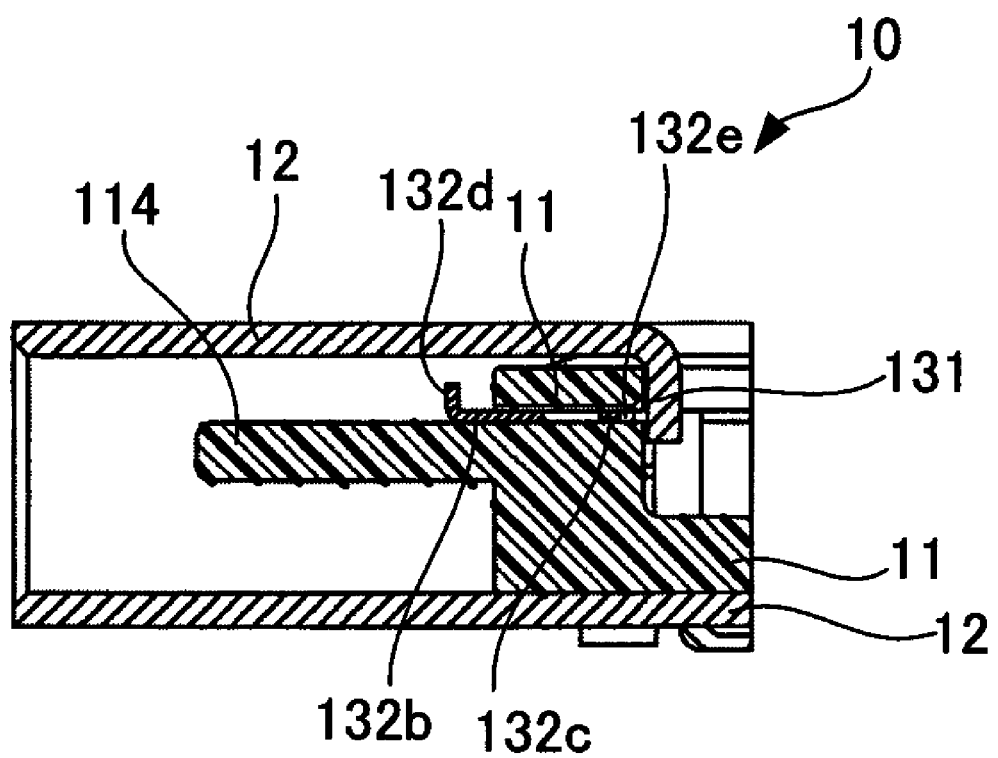
FIG. 2 is a vertical cross-sectional view of the connector taken along s line 2-2 in FIG. 1b.
Figure 3:
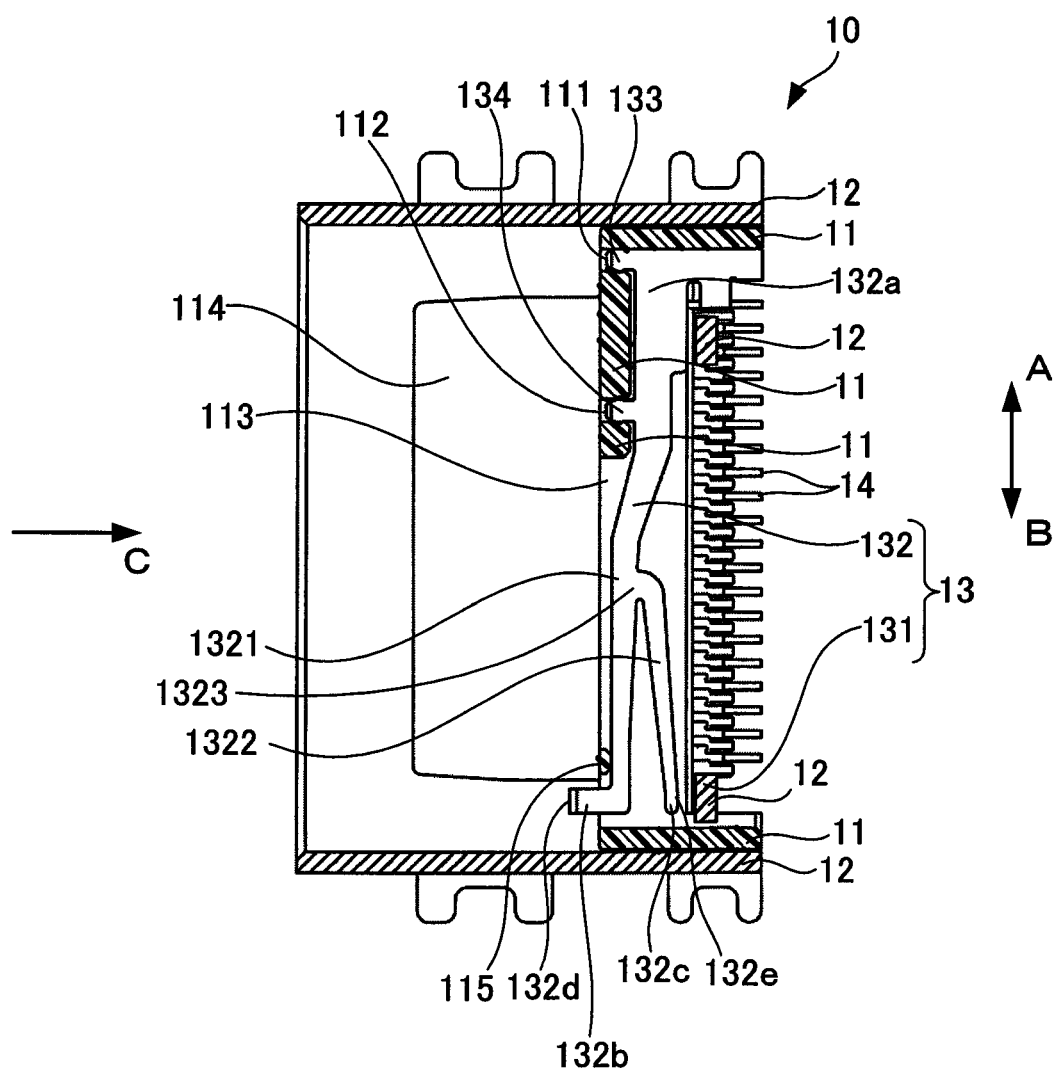
FIG. 3 is a lateral cross-sectional view taken along a line 3-3 in FIG. 1c.

As illustrated in FIG. 1 through FIG. 3, a connector 10 includes an insulating housing 11 made of, for example, resin and having a platform section 114 to be mated with a mating connector (not shown), a metal shell 12 covering the insulating housing 11, and a switch 13 that detects mating with the mating connector. In the insulating housing 11, multiple signal contacts 14 are housed while being aligned in a single row. Further, the switch 13 includes a fixed contact 131 and a movable contact 132.

The fixed contact 131 is formed by bending a part of a rear end of a top surface 121 of the metal shell 12 downward. Since the fixed contact 131, of the fixed contact 131 and the movable contact 132 included in the switch 13, is made of the part of the shell 12, the number of components is smaller than that of the conventional connector, in which both of the pair of contacts forming the switch 13 are provided as separate components from connector components other than these contacts. This design contributes to reduction in cost.

A part near one end of the movable contact 132, in a width direction (a direction indicated by an arrow AB in FIG. 3) of the insulating housing 11, is a fixed end 132a that is held by this insulating housing 11. In other words, the movable contact 132 is fixed to the insulating housing 11 when holding protrusions 133 and 134 of the fixed end 132a are press-fitted into receiving passageways 111 and 112 of the housing 11. Further, the movable contact 132 extends from the fixed end 132a to a point near the other end, in the width direction of the insulating housing 11. The movable contact 132 bifurcates into two at an approximately midpoint in the extension, and divides, near the other end in the width direction, of the respective two serve as free ends 132b and 132c.

The free end 132b, which is one of the two free ends 132b and 132c in the movable contact 132, has an attachment section 132d that abuts the mating connector (see FIG. 5) that has approached in a mating direction (a direction indicated by an arrow C in FIG. 3). This attachment section 132d is located near the other end in the width direction of the insulating housing 11.

Furthermore, the free end 132c, which is the other of the two free ends 132b and 132c in the movable contact 132, is a contacting section 132e that contacts the fixed contact 131 when the attachment section 132d is pushed by the mating connector. This contacting section 132e is located near the other end in the width direction of the insulating housing 11.

In the movable contact 132, a part that extends from the fixed end 132a to the free end 132b having the attachment section 132d is referred to as a front beam 1321. Further, in the movable contact 132, a part that extends from a bifurcation part 1323 to the free end 132c having the contacting section 132e is referred to as a rear beam 1322.

In the connector 10 with the switch 13, the length of the rear beam 1322 is determined according to the position of the bifurcation part 1323 and setting of an angle of bifurcation and thus, the length of the rear beam 1322 may be a desired length. Further, the connector 10 with the switch 13 is designed so that the rear beam 1322 has satisfactory flexibility by providing the rear beam 1322 with the desired length. Furthermore, the connector 10 with the switch 13 is designed so that each of the attachment section 132d in the front beam 1321 and the contacting section 132e in the rear beam 1322 has a satisfactory amount of displacement.

The movable contact 132 described above is a member formed by stamping a metal plate and then forming the attachment section 132d. In other words, the movable contact 132 is formed flat except for the attachment section 132d. Thus, the movable contact 132 is design in such a way to minimize space used, and the movable contact 132, except the attachment section 132d, may be accommodated in a narrow slit 113 of the insulating housing 11 accordingly. This design contributes to reductions in size and cost of the connector 10 with the switch 13.

Incidentally, the insulating housing 11 is provided with a positioning section 115 to be abutted by a leading edge near the free end 132b of the front beam 1321. Because this positioning section 115 abuts the front beam 1321, the position of the attachment section 132d may be controlled precisely.

Next, with reference to FIG. 4 and FIG. 5, an operation of the switch 13 when a mating connector 20 is mated with the connector 10 with the switch 13 described with reference to FIG. 1 through FIG. 3. Further, FIG. 4 illustrates how a part of the mating connector 20 mates with the connector 10 with the switch 13.

Figure 4:
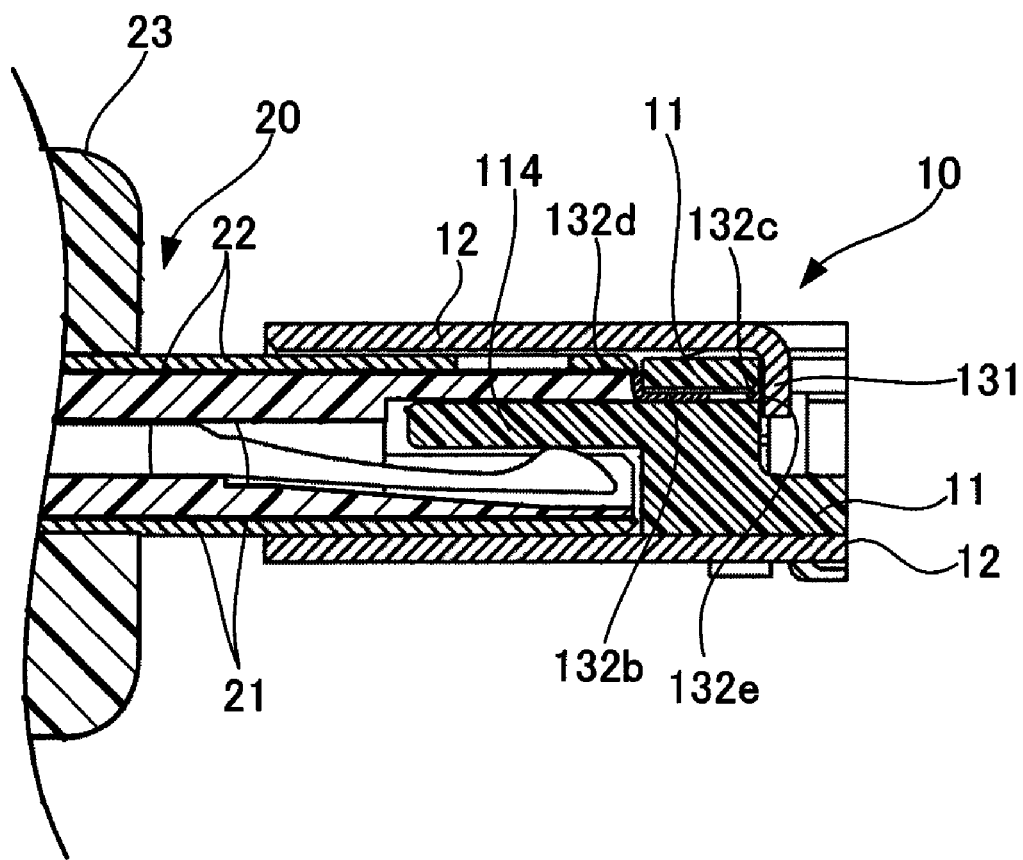
FIG. 4 a vertical cross-sectional view of the connector taken along s line 2-2 in FIG. 1b in a state in which a mating connector is mated with the connector according to the invention.
Figure 5:
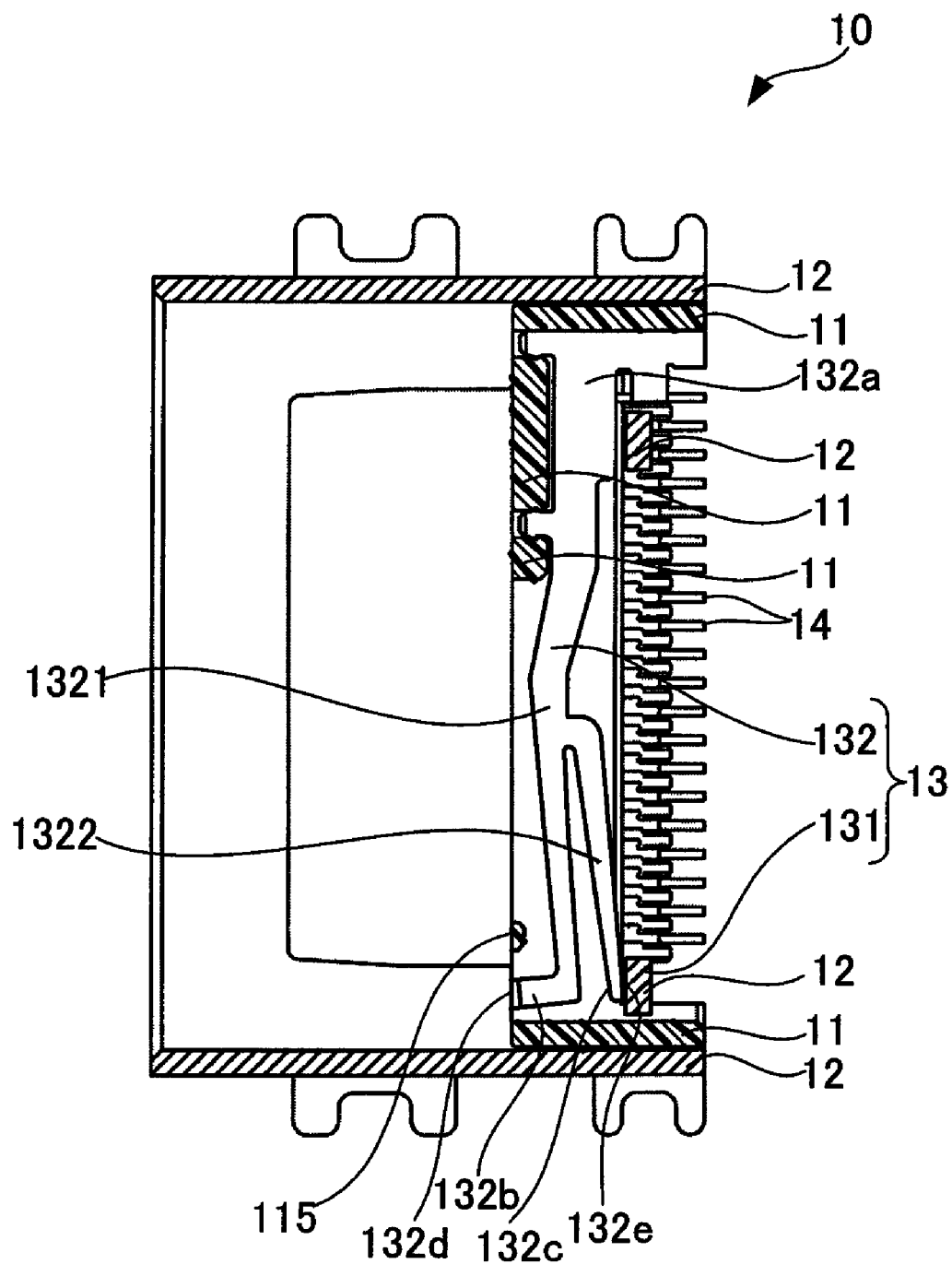
FIG. 5 is a lateral cross-sectional view taken along a line 3-3 in FIG. 1c in the state in which the mating connector is mated with the connector according to the invention.

As illustrated in FIG. 4, the mating connector 20 includes an insulating housing 21 made of, for example, resin, which is mated with the insulating housing 11 of the connector 10 with the switch 13. The mating connector 20 further includes a metal shell 22 that covers the insulating housing 21 and an over mold resin 23 that covers base parts of the insulating housing 21 and the shell 22.

When the mating connector 20 is inserted into the connector 10 with the switch 13, at first, the attachment section 132d of the front beam 1321 in the movable contact 132 is biased by the insulating housing 21 of the mating connector 20, and the entire front beam 1321 flexes. Further, along with the flexing of the entire front beam 1321, the contacting section 132e of the rear beam 1322 in the movable contact 132 approaches the fixed contact 131, and when the mating connector 20 is mated, the contacting section 132e contacts the fixed contact 131 as shown in FIG. 4 and FIG. 5.

As described above, a design is achieved so that the rear beam 1322 has appropriate flexibility and thus, there is no need to provide flexibility of the fixed contact 131 to be contacted by the contacting section 132e of the rear beam 1322. In other words, flexible space of the fixed contact 131 is unnecessary and thus, minimizing the space of the switch 13 may be obtained. Therefore, the switch 13 contributes to a reduction in size of the connector 10 with the switch 13.

Further, plastic deformation due to repeated use is minimized because the rear beam 1322 has satisfactory flexibility. Furthermore, due to the flexibility, the rear beam 1322 reduces damage to the fixed contact 131, which occurs when the contacting section 132e of the rear beam 1322 contacts the fixed contact 131. Therefore, durability and contact reliability of the connector 10 with the switch 13 according to the invention is high.

Still further, in the embodiment shown, because the rear beam 1322 has satisfactory flexibility, contact reliability of the switch 13 is ensured thanks to the satisfactory flexibility of the switch 13 even in a state, for example, in which a mechanical load such as vibration or shock is applied to the connector 10 with the switch 13. Moreover, due to the flexibility, the rear beam 1322 having satisfactory flexibility may accommodate an error of an insertion depth of the mating connector 20 being inserted and thus, contact reliability is high in this regard as well.

The foregoing illustrates some of the possibilities for practicing the invention. Many other embodiments are possible within the scope and spirit of the invention. It is, therefore, intended that the foregoing description be regarded as illustrative rather than limiting, and that the scope of the invention is given by the appended claims together with their full range of equivalents.

What is claimed is:

1. A connector, comprising:
   an insulating housing;
   a metal shell covering the insulative housing; and
   a switch having a fixed contact and a movable contact, the fixed contact being formed by a part of the shell, the movable contact having a fixed end being held by the insulative housing;
   wherein the movable contact includes a bifurcation part at an approximate midpoint of the movable contact that bifurcates into an attachment section for being abutted and then pushed by a mating connector when the mating connector connects from a mating direction and a contacting section.

2. The connector according to claim 1, wherein the movable contact is flat except for the attachment section.

3. The connector according to claim 1, wherein the contacting section contacts the fixed contact when the mating connector pushes the attachment section.

4. The connector according to claim 1, wherein the fixed end is positioned near one end in a width direction of the insulative housing.

5. The connector according to claim 4, wherein the movable contact extends from the fixed end to a position being within close proximity to an opposite end in the width direction of the insulative housing.

6. The connector according to claim 5, wherein the attachment section and the contacting section are positioned to be being within close proximity to the opposite end.

7. The connector according to claim 1, wherein the movable contact is secured to the insulating housing by at least one holding protrusion.

8. The connector according to claim 7, further comprising at least one receiving passageway in the insulative housing.

9. The connector according to claim 8, wherein the at least one holding protrusion is press-fitted into the at least one receiving passageway.

10. The connector according to claim 1, further comprising a front beam that extends from the fixed end to the attachment section.

11. The connector according to claim 10, further comprising a rear beam that extends from the bifurcation part to the contacting section.

12. The connector according to claim 11, wherein a length of the rear beam is determined by a position of the bifurcation part with respect to the fixed end.

13. The connector according to claim 12, wherein a length of the rear beam is determined by an angle of the bifurcation part with respect to the front beam.

14. A connector for mating with a mating connector, comprising:
   an insulating housing;
   a metal shell that covers the insulative housing; and
   a switch having a fixed contact and a movable contact, the switch detecting connection with the mating connector;
   wherein the fixed contact is formed by a part of the shell;
   wherein the movable contact extends from a fixed end being held by the insulative housing and bifurcates at an approximate midpoint of the movable contact into an attachment section for being abutted and then pushed by a mating connector when the mating connector connects from a mating direction and a contacting section.

15. The connector according to claim 14, wherein the contacting section contacts the fixed contact when the mating connector pushes the attachment section.

16. The connector according to claim 14, wherein the mating connector includes an insulating housing and a metal shell that covers the insulating housing.

17. The connector according to claim 16, wherein the mating connector further includes an over mold resin that covers base parts of the insulating housing and the shell.

18. The connector according to claim 17, wherein a front beam of the attachment section is biased by the insulating housing when the mating connector is inserted into the connector.

19. The connector according to claim 18, wherein a rear beam of a contacting section approaches the fixed contact when the front beam flexes.

20. The connector according to claim 19, wherein the rear beam contacts the fixed contact when the mating connector mates with the connector.

* * * * *